(12) United States Patent
Nagasawa et al.

(10) Patent No.: US 9,033,574 B2
(45) Date of Patent: May 19, 2015

(54) THERMAL ANALYZER

(71) Applicant: Hitachi High-Technologies Corporation, Minato-ku, Tokyo (JP)

(72) Inventors: Kanji Nagasawa, Chiba (JP); Kentaro Yamada, Chiba (JP); Shinya Nishimura, Chiba (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 269 days.

(21) Appl. No.: 13/777,291

(22) Filed: Feb. 26, 2013

(65) Prior Publication Data
US 2013/0235899 A1 Sep. 12, 2013

(30) Foreign Application Priority Data

Mar. 6, 2012 (JP) ................................. 2012-048710

(51) Int. Cl.
*G01N 25/00* (2006.01)
*G01N 25/02* (2006.01)
*G01N 5/00* (2006.01)

(52) U.S. Cl.
CPC ................ *G01N 25/00* (2013.01); *G01N 25/02* (2013.01); *G01N 5/00* (2013.01)

(58) Field of Classification Search
USPC .............................................. 374/10–14, 31
See application file for complete search history.

(56) References Cited

U.S. PATENT DOCUMENTS

| 5,321,719 | A | * | 6/1994 | Reed et al. ....................... 374/14 |
| 5,588,746 | A | * | 12/1996 | Minobe et al. .................. 374/10 |
| 6,390,674 | B1 | * | 5/2002 | Nakamura et al. ............ 374/187 |
| 2003/0086471 | A1 | * | 5/2003 | Nakatani et al. ................ 374/14 |
| 2005/0025212 | A1 | * | 2/2005 | Carter et al. ....................... 374/1 |
| 2005/0123020 | A1 | * | 6/2005 | Nakamura ....................... 374/14 |
| 2007/0201533 | A1 | * | 8/2007 | Takeuchi et al. ................ 374/14 |

* cited by examiner

*Primary Examiner* — Mirellys Jagan
(74) *Attorney, Agent, or Firm* — Brinks Gilson & Lione (57) ABSTRACT

A thermal analyzer (100) includes: a furnace tube (9) made of a transparent material; a heating furnace (3); a sample holding part (41, 42) arranged inside the furnace tube; a first support base (12); a second support base (14); a measurement chamber (30) connected to the furnace tube; a first movement part (22) for moving the first support base and the second support base between a measurement position, at which the furnace tube is connected to the measurement chamber, and a sample setting position, at which the sample holding part is exposed on a rear end side with respect to the furnace tube and the heating furnace; and a second movement part (24) for moving only the second support base to a sample observation position, at which the heating furnace is advanced and the furnace tube is exposed. Accordingly, the sample is observable from outside the exposed furnace tube.

6 Claims, 10 Drawing Sheets

THERMAL ANALYZER

RELATED APPLICATIONS

This application claims priority under 35 U.S.C. §119 to Japanese Patent Application No. 2012-048710 filed on Mar. 6, 2012, the entire content of which is hereby incorporated by reference.

BACKGROUND OF THE INVENTION

1. Field of the Invention

The present invention relates to a thermal analyzer for measuring a physical change of a sample along with its temperature change caused by heating the sample.

2. Description of the Related Art

Conventionally, as a technique of evaluating temperature characteristics of a sample, there has been employed a technique called thermal analysis for measuring a physical change of a sample along with its temperature change caused by heating the sample. The thermal analysis includes all such techniques defined in JIS K 0129:2005 "General rules for thermal analysis," for measuring physical properties of a measurement target (sample) obtained when the temperature of the sample is controlled based on a program. In general, the thermal analysis is typified by the following five methods: (1) Differential Thermal Analysis (DTA) for detecting a temperature (temperature difference), (2) Differential Scanning calorimetry (DSC) for detecting a heat flow difference, (3) Thermogravimetry (TG) for detecting a mass (weight change), (4) Thermomechanical Analysis (TMA) for detecting mechanical characteristics, and (5) Dynamic Mechanical Analysis (DMA).

Figure 8:
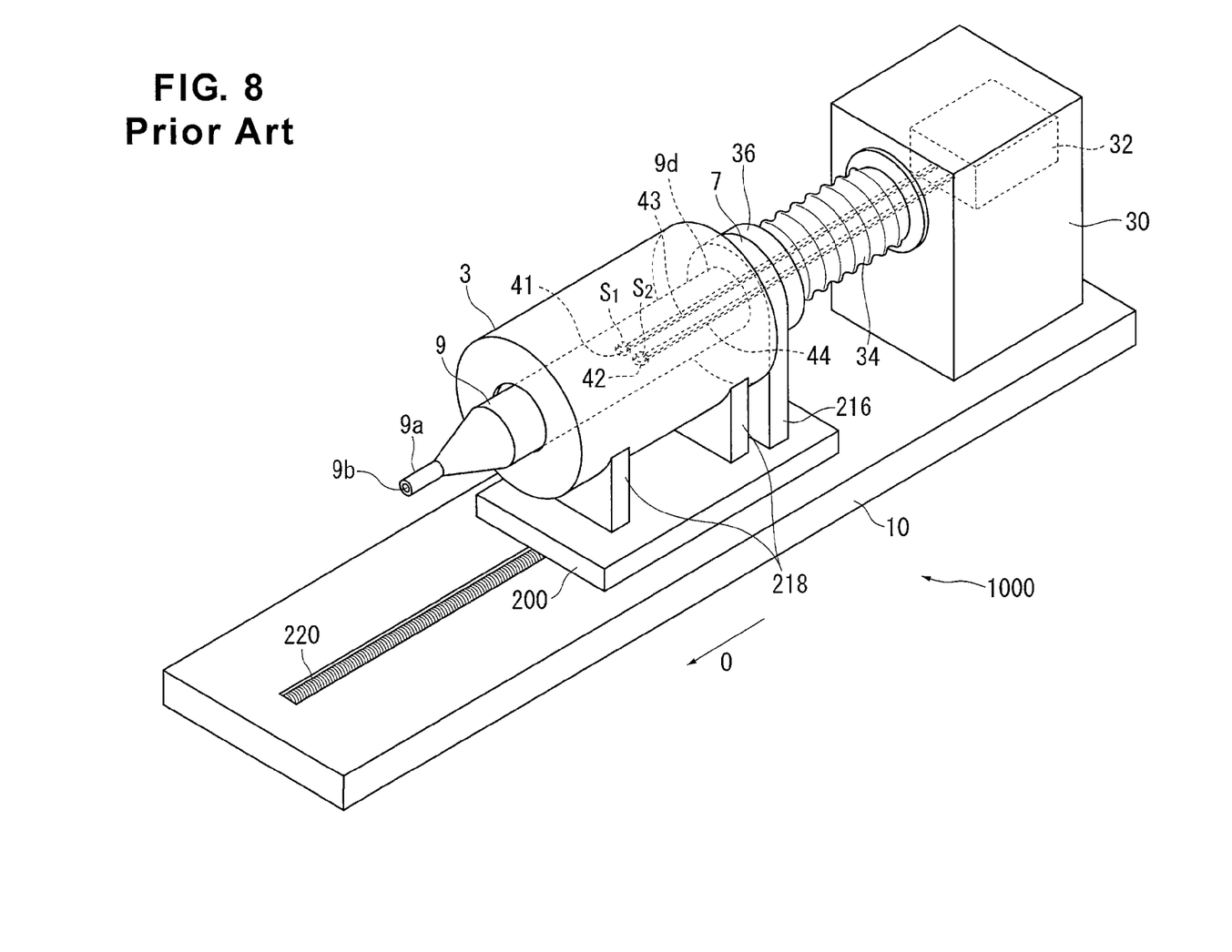
FIG. 8 is a perspective view illustrating a conventional thermogravimetry (TG) apparatus.

For example, as illustrated in FIG. 8, as a thermal analyzer 1000 for performing the above-mentioned thermogravimetry (TG), there is known a thermal analyzer including a furnace tube 9 which is formed into a cylindrical shape and has a gas discharge port 9b which is reduced in diameter and is arranged at a tip end portion 9a thereof, a cylindrical heating furnace 3 which externally surrounds the furnace tube 9, sample holders 41 and 42 which are arranged inside the furnace tube 9 and hold samples $S_1$ and $S_2$, respectively, a measurement chamber 30 which is hermetically connected to a rear end portion 9d of the furnace tube 9, and a weight detector 32 which is arranged inside the measurement chamber 30 and measures weight changes of the samples (see, for example, Japanese Patent Application Laid-open Nos. Hei 11-326249, 2007-232479, and Hei 7-146262). In addition, two support columns 218 extend downward from a lower end of the heating furnace 3, and are connected to a support base 200. Further, a flange part 7 is fixed on the outer side of the rear end portion 9d of the furnace tube 9. A single support column 216 extends downward from a lower end of the flange part 7, and is also connected to the support base 200. The support base 200 and the measurement chamber 30 are placed on a base 10, and the support base 200 is reciprocable by a linear actuator 220 in an axial direction O of the furnace tube 9.

The heating furnace 3 heats the sample holders 41 and 42 from outside the furnace tube 9, and the weight detector 32 may therefore detect weight changes of the samples $S_1$ and $S_2$ along with their temperature changes.

Figure 9:
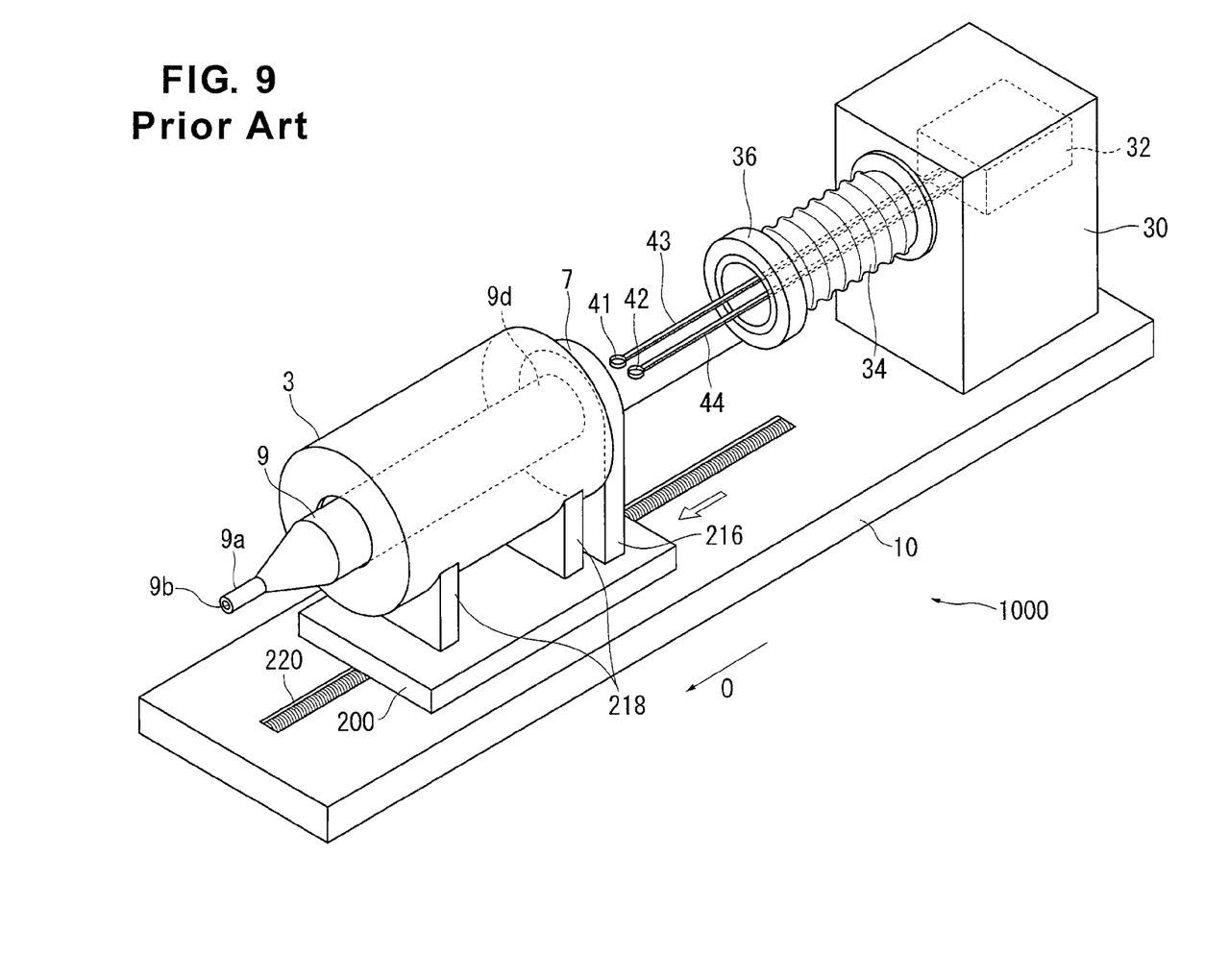
FIG. 9 is a view illustrating an embodiment in which samples are set or replaced in the conventional thermogravimetry (TG) apparatus.

As illustrated in FIG. 9, when setting the samples $S_1$ and $S_2$ onto the respective sample holders 41 and 42 or replacing the samples $S_1$ and $S_2$, the linear actuator 220 advances the support base 200 toward the tip end of the furnace tube 9 (left side of FIG. 9), and also advances the heating furnace 3 and the furnace tube 9 which are fixed to the support base 200. Accordingly, the sample holders 41 and 42 are exposed on the rear end side with respect to the furnace tube 9 so that the samples $S_1$ and $S_2$ can be set or replaced.

By the way, when the above-mentioned thermal analyzer is used, it is possible to detect values of necessary thermophysical properties, but there arises a problem in that the changes of the samples during the thermal analysis cannot visually be observed. This is because the furnace tube 9 is generally made of ceramics such as sintered alumina or a heat-resistant metal such as Inconel (trademark), and the heating furnace 3 covers the furnace tube 9.

SUMMARY OF THE INVENTION

The present invention has been made to solve the above-mentioned problem, and therefore provides a thermal analyzer which enables observation of a change of a sample during a thermal analysis.

In order to solve the above-mentioned problem, according to an exemplary embodiment of the present invention, there is provided a thermal analyzer, including: a furnace tube which is made of a transparent material and is formed into a cylindrical shape, the furnace tube having a gas discharge port which is reduced in diameter and is arranged at a tip end portion thereof in an axial direction; a heating furnace which has a cylindrical shape and externally surrounds the furnace tube; sample holding means for holding a sample, the sample holding means being arranged inside the furnace tube; a first support base; a second support base; a furnace tube fixing part for fixing a rear end portion of the furnace tube in the axial direction to the first support base; a heating furnace fixing part for fixing the heating furnace to the second support base; a measurement chamber which is hermetically connected to the rear end portion of the furnace tube; measurement means for measuring a change in physical properties of the sample, the measurement means being arranged inside the measurement chamber; first movement means for moving the first support base and the second support base between a measurement position, at which the rear end portion of the furnace tube is connected to the measurement chamber and the sample holding means is covered with the heating furnace, and a sample setting position, at which the furnace tube and the heating furnace are advanced toward a tip end side with respect to the measurement position and the sample holding means is exposed on a rear end side with respect to the furnace tube and the heating furnace; and second movement means for moving only the second support base to a sample observation position, at which the heating furnace is advanced toward the tip end side with respect to the measurement position under a state in which the rear end portion of the furnace tube is connected to the measurement chamber, and the furnace tube is exposed in a region including the sample holding means. The thermal analyzer is configured to enable observation of the sample from outside the exposed furnace tube at the sample observation position.

According to this thermal analyzer, it is possible to observe the sample during the thermal analysis at the sample observation position, as well as to measure the sample at the measurement position and set the sample at the sample setting position in the same manner as in the conventional thermal analyzer.

The second support base may be placed on the first support base, and when the first movement means moves the first support base, the second support base may move integrally with the first support base.

According to this thermal analyzer, it is possible to move the furnace tube and the heating furnace integrally to the measurement position and the sample setting position with high reliability.

It is preferred that the furnace tube be made of one of quartz glass and sapphire glass because the heat-resistant temperature thereof is high.

The thermal analyzer may further include a heat conductive member which covers at least a part of the exposed furnace tube at the sample observation position to transfer heat of the heating furnace.

With this structure, the heat of the heating furnace is transferred from the heat conductive member to the exposed portion of the furnace tube, and hence the sample can be observed while maintaining the heated state.

It is preferred that the heat conductive member have a thermal conductivity of 50 W/(m·K) or more.

The thermal analyzer may further include a heat insulating member which covers at least a part of the heat conductive member.

With this structure, the temperature of the exposed portion of the furnace tube is not easily lowered, and hence the sample can be observed while maintaining the heated state with higher reliability.

According to the present invention, it is possible to obtain the thermal analyzer which enables observation of the change of the sample during the thermal analysis.

DETAILED DESCRIPTION OF THE PREFERRED EMBODIMENTS

In the following, an embodiment of the present invention is described with reference to the accompanying drawings. Note that, a tip end portion 9a side of a furnace tube 9 along an axial direction O is referred to as "tip end (side)," and the opposite side is referred to as "rear end (side)."

Figure 1:
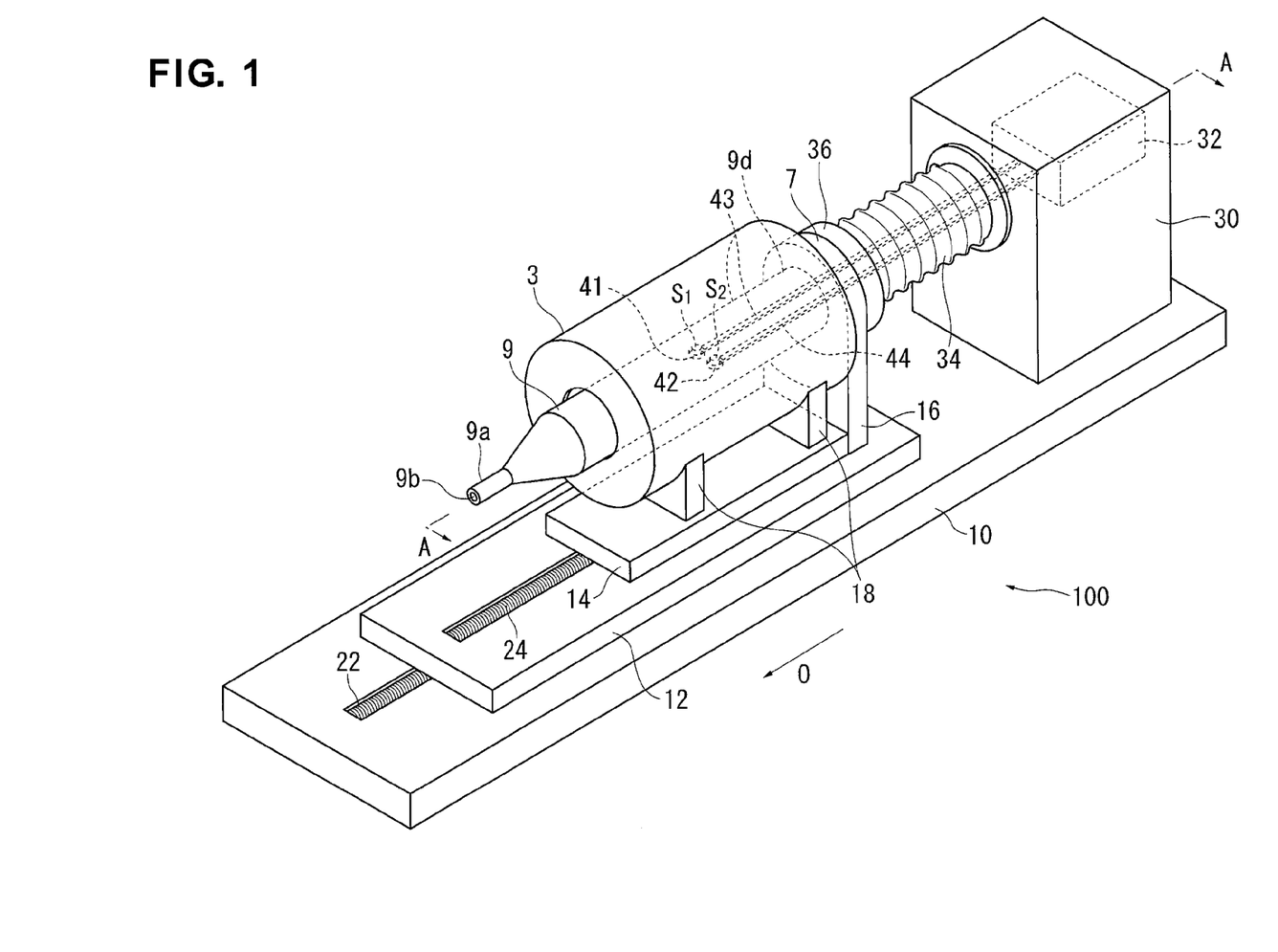
FIG. 1 is a perspective view illustrating a structure of a thermal analyzer according to an embodiment of the present invention at a measurement position.
Figure 2:
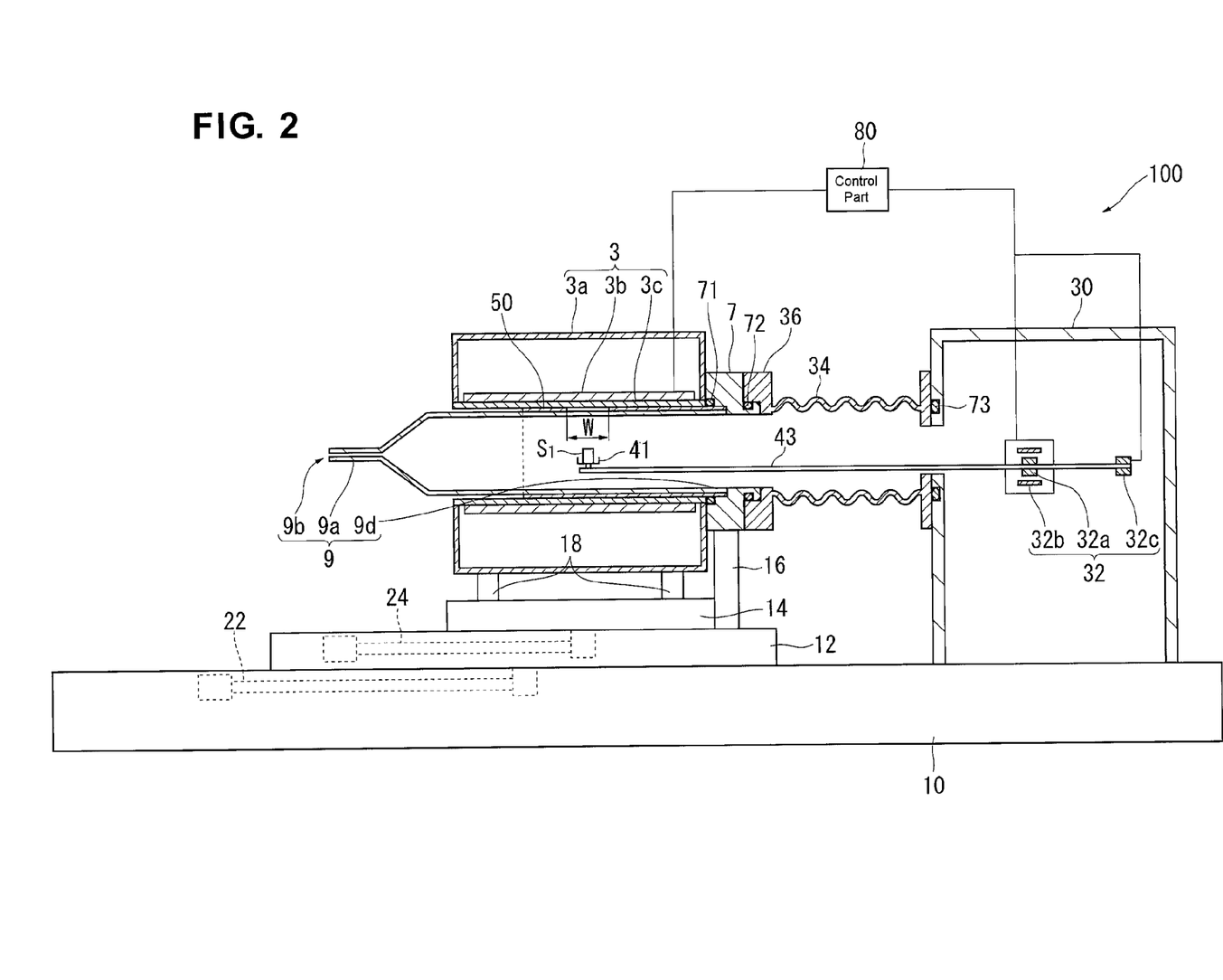
FIG. 2 is a sectional view taken along the line A-A of FIG. 1.

FIG. 1 is a perspective view illustrating a structure of a thermal analyzer 100 according to the embodiment of the present invention. FIG. 2 is a sectional view taken along the line A-A of FIG. 1.

The thermal analyzer 100 serves as a thermogravimetry (TG) apparatus, and includes the cylindrical furnace tube 9, a cylindrical heating furnace 3 which externally surrounds the furnace tube 9, sample holders (corresponding to "sample holding means" in the claims) 41 and 42 which are arranged inside the furnace tube 9 and hold samples $S_1$ and $S_2$, respectively, a first support base 12, a second support base 14 placed on a top surface of the first support base 12, a measurement chamber 30 which is connected to a rear end portion 9d of the furnace tube 9 in the axial direction O, a weight detector (corresponding to "measurement means" in the claims) 32 which is arranged inside the measurement chamber 30 and measures weight changes of the samples $S_1$ and $S_2$, and a base 10 having a top surface on which the first support base 12 and the measurement chamber 30 are placed.

In addition, two support columns (corresponding to a "heating furnace fixing part" in the claims) 18 extend downward from a lower end of the heating furnace 3 in the vicinity of both axial ends thereof, and are connected to a top surface of the second support base 14. Further, a flange part 7 is fixed on the outer side of the rear end portion 9d of the furnace tube 9, and a single support column (corresponding to a "furnace tube fixing part" in the claims) 16 extends downward from a lower end of the flange part 7. The support column 16 is connected to the top surface of the first support base 12. Note that, the support column 16 is arranged on the rear end side with respect to a rear end of the second support base 14, and does not interfere with the second support base 14.

Further, a groove is formed in the base 10 along the axial direction O, and a linear actuator (corresponding to "first movement means" in the claims) 22 is arranged in the groove. The rear end side of the linear actuator 22 is connected to the first support base 12, and the tip end side (or servomotor on the tip end side) is connected to the base 10. The first support base 12 is reciprocable by the linear actuator 22 in the axial direction O along the above-mentioned groove.

Further, a groove is formed in the first support base 12 along the axial direction O, and a linear actuator (corresponding to "second movement means" in the claims) 24 is arranged in the groove. The rear end side of the linear actuator 24 is connected to the second support base 14, and the tip end side (or servomotor on the tip end side) is connected to the first support base 12. The second support base 14 is reciprocable by the linear actuator 24 in the axial direction O along the groove of the first support base 12.

The linear actuators 22 and 24 are each formed of, for example, a ball screw and a servomotor, but any publicly known actuator which is linearly driven in the axial direction O may be used therefor.

The heating furnace 3 includes a cylindrical core tube 3c forming an inner surface of the heating furnace 3, a heater 3b fitted onto the core tube 3c, and a cylindrical outer cylinder 3a having side walls on both ends thereof (see FIG. 2). At the center of each side wall of the outer cylinder 3a, a center hole is provided so as to insert the core tube 3c therethrough. The outer cylinder 3a surrounds the heater 3b to maintain the temperature of the heating furnace 3, and the outer cylinder 3a may be provided with an adjustment hole (not shown) as appropriate to adjust the temperature of the heating furnace 3. Note that, the inner diameter of the core tube 3c is larger than the outer diameter of the furnace tube 9, and the heating furnace 3 is configured to heat the furnace tube 9 (and samples $S_1$ and $S_2$ inside the furnace tube 9) in a non-contact manner.

The furnace tube 9 is reduced in diameter to have a tapered shape toward the tip end portion 9a. The tip end portion 9a is formed into an elongated capillary shape, and has a gas discharge port 9b opened at its tip end. A purge gas is introduced into the furnace tube 9 from the rear end side as appropriate, and the purge gas, decomposition products generated from the samples due to heating, and the like are discharged to the outside through the gas discharge port 9b. On the other hand, on the outer side of the rear end portion 9d of the furnace tube 9, the ring-like flange part 7 is fixed through an intermediation of a seal member 71 (see FIG. 2).

Further, the furnace tube 9 is made of a transparent material, and hence the samples $S_1$ and $S_2$ are observable from outside the furnace tube 9. The transparent material herein refers to a material which allows visible light to pass therethrough at a predetermined light transmittance, and includes a semi-transparent material. Further, as the transparent material, quartz glass or sapphire glass may be used suitably.

Note that, as illustrated in FIG. 2, the rear end side of the furnace tube 9 is covered with a copper heat conductive member 50 described in detail later, and the seal member 71 is arranged on the outer side of the heat conductive member 50 to fix the heat conductive member 50 to the furnace tube 9.

Balance arms 43 and 44 extending in the axial direction O toward the rear end side are connected to the sample holders 41 and 42, respectively, and the balance arms 43 and 44 are arranged in a horizontal direction. The samples $S_1$ and $S_2$ are placed on the sample holders 41 and 42 through an intermediation of sample containers (not shown), respectively. In this case, the sample $S_1$ is a measurement sample (sample) and the sample $S_2$ is a reference substance (reference). Further, thermocouples are arranged immediately below the sample holders 41 and 42, and hence the temperatures of the samples can be measured. The balance arms 43 and 44, the sample holders 41 and 42, and the sample containers (not shown) are each made of, for example, platinum.

The measurement chamber 30 is arranged at the rear end of the furnace tube 9, and a tube-like bellows 34 extending in the axial direction O toward the tip end side of the furnace tube 9 is fixed to the tip end portion of the measurement chamber 30 through an intermediation of a seal member 73. The tip end side of the bellows 34 forms a flange part 36, and the flange part 36 is hermetically connected to the flange part 7 through an intermediation of a seal member 72. In this manner, the measurement chamber 30 and the furnace tube 9 communicate internally to each other, and the rear ends of the balance arms 43 and 44 extend to the interior of the measurement chamber 30 through the furnace tube 9. Note that, as the seal members 71 to 73, for example, an O-ring or a gasket may be used.

As illustrated in FIG. 2, the weight detector 32 arranged inside the measurement chamber 30 includes coils 32a, magnets 32b, and position detecting parts 32c. The position detecting parts 32c are each formed of, for example, a photosensor, and are arranged on the rear end side of the balance arms 43 and 44 to detect whether or not the balance arms 43 and 44 are held in a horizontal state. On the other hand, the coils 32a are fixed to axial centers (fulcrums) of the balance arms 43 and 44, respectively, and the magnets 32b are arranged on both sides of each coil 32a. A current is caused to flow through the coils 32a so that the balance arms 43 and 44 assume a horizontal state, and the current is measured, to thereby measure the weights of the respective samples $S_1$ and $S_2$ at the tip ends of the balance arms 43 and 44. Note that, the weight detector 32 is provided to each of the balance arms 43 and 44.

Further, as illustrated in FIG. 2, the linear actuators 22 and 24, the heater 3b, and the weight detector 32 are controlled by a control part 80 formed of, for example, a computer. Specifically, the control part 80 controls the power feed to the heater 3b to heat the furnace tube 9 (sample holders 41 and 42) in a predetermined heating pattern, and acquires temperature changes and weight changes of the samples $S_1$ and $S_2$ at this time from the weight detector 32. Further, the control part 80 controls the operations of the linear actuators 22 and 24 to move the heating furnace 3 and the furnace tube 9 to a measurement position, a sample setting position, and a sample observation position described later.

Note that, the "measurement position" refers to such a position that the flange part 36 and the flange part 7 are hermetically connected to each other and the heating furnace 3 covers the sample holders 41 and 42 (that is, samples $S_1$ and $S_2$) of the furnace tube 9.

Figure 3:
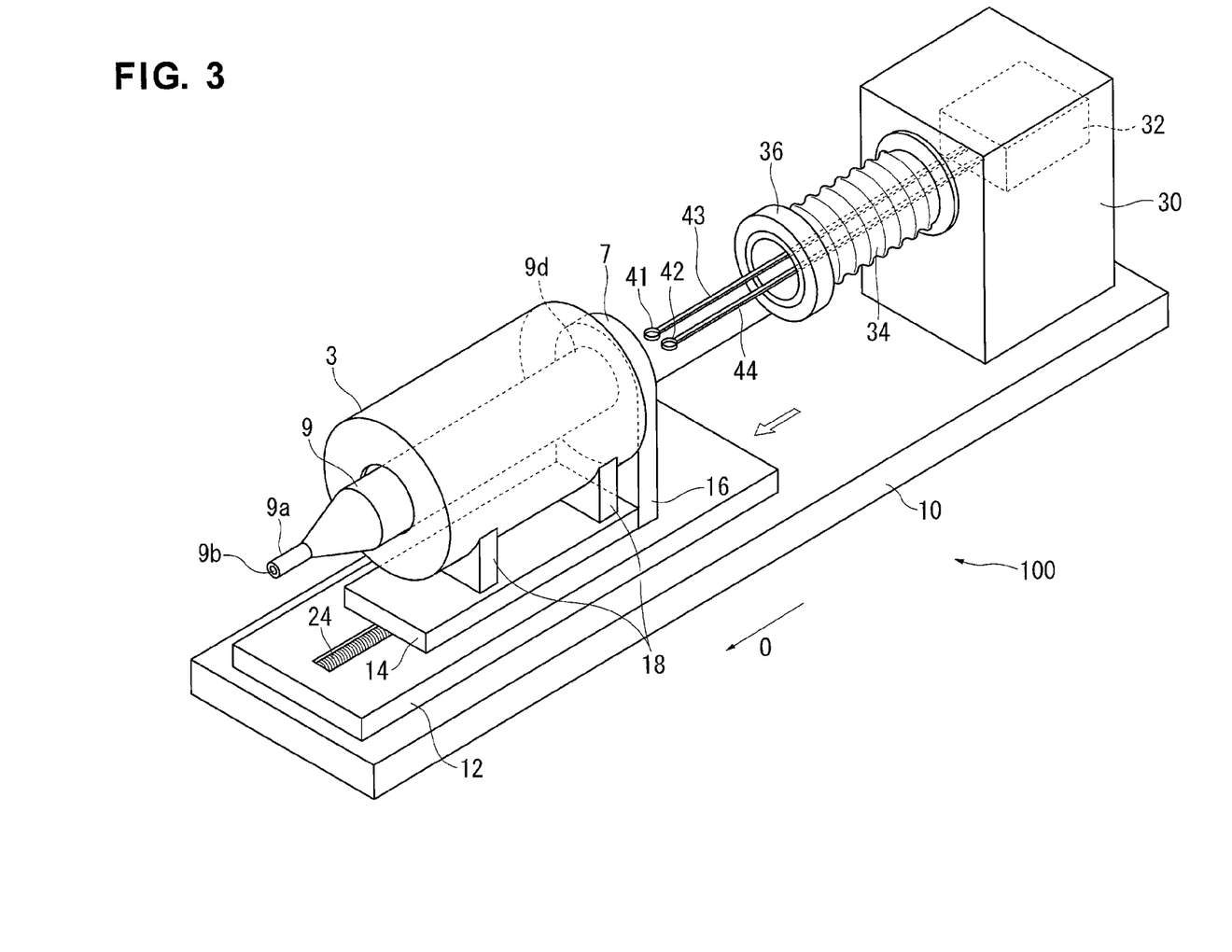
FIG. 3 is a view illustrating positions of a heating furnace and a furnace tube at a sample setting position.

FIG. 3 illustrates positions of the heating furnace 3 and the furnace tube 9 in a case of setting the samples $S_1$ and $S_2$ onto the sample holders 41 and 42 or replacing the samples $S_1$ and $S_2$. When setting (placing) or replacing the samples $S_1$ and $S_2$, the second support base 14 is not moved but maintained at the measurement position (see FIGS. 1 and 2), and only the first support base 12 is advanced by the linear actuator 22 toward the tip end side of the furnace tube 9 (left side of FIG. 3). Then, the first support base 12 and the second support base 14 move integrally with each other. Accordingly, when the furnace tube 9 and the heating furnace 3 respectively fixed to the first support base 12 and the second support base 14 are advanced toward the tip end side with respect to the above-mentioned measurement position, the sample holders 41 and 42 are exposed on the rear end side with respect to the furnace tube 9 and the heating furnace 3 so that the samples $S_1$ and $S_2$ can be set or replaced.

The "sample setting position" herein refers to such a position that, as illustrated in FIG. 3, the flange part 36 and the flange part 7 are separated from each other in the axial direction O and the sample holders 41 and 42 (that is, samples $S_1$ and $S_2$) are exposed on the rear end side with respect to the furnace tube 9 and the heating furnace 3.

Figure 4:
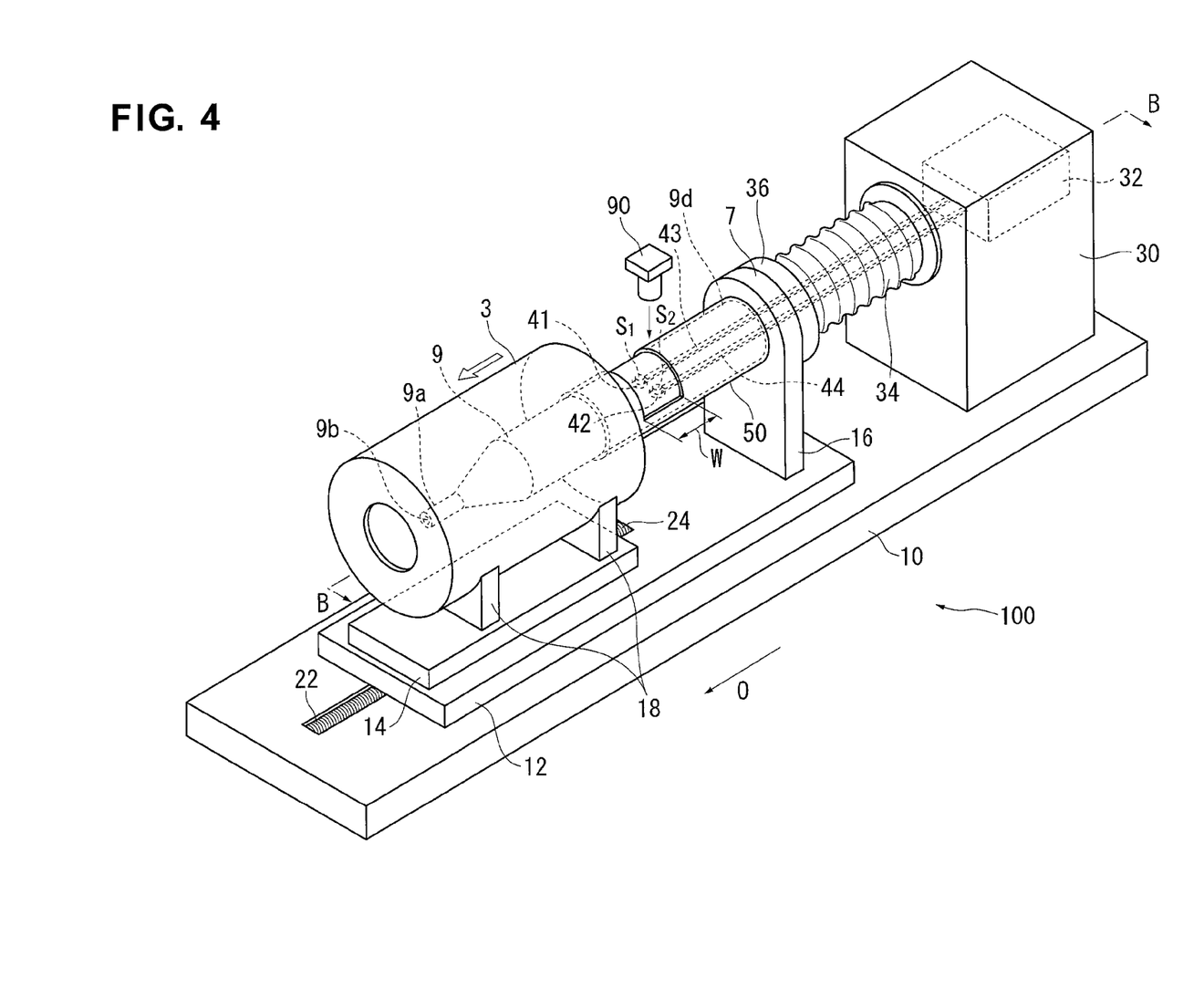
FIG. 4 is a view illustrating positions of the heating furnace and the furnace tube at a sample observation position.

Next, referring to FIG. 4, features of the present invention are described. As illustrated in FIG. 4, when the heating furnace 3 is advanced toward the tip end side with respect to the above-mentioned measurement position under a state in which the flange part 36 and the flange part 7 are connected to each other, the furnace tube 9 is exposed in a region including the sample holders 41 and 42 (that is, samples $S_1$ and $S_2$). Accordingly, the changes of the samples $S_1$ and $S_2$ during the thermal analysis can be observed through the furnace tube 9.

Specifically, the samples $S_1$ and $S_2$ are first heated by the heating furnace 3 at the measurement position illustrated in FIG. 1. After that, the first support base 12 is not moved but maintained at the measurement position (see FIGS. 1 and 2), and only the second support base 14 is advanced by the linear actuator 24 toward the tip end side of the furnace tube 9 (left side of FIG. 3) until the heating furnace 3 is situated on the tip end side with respect to the sample holders 41 and 42. Accordingly, the samples $S_1$ and $S_2$ during the thermal analysis can be observed. For example, in the example of FIG. 4, imaging means (for example, camera or optical microscope) 90 is arranged above the furnace tube 9 that is exposed on the rear end side of the heating furnace 3, to thereby observe the samples $S_1$ and $S_2$ during the thermal analysis.

Note that, the "sample observation position" refers to such a position that, as illustrated in FIG. 4, the heating furnace 3 is advanced toward the tip end side with respect to the measurement position under the state in which the flange part 36 and the flange part 7 are connected to each other, and the furnace tube 9 is exposed in the region including the sample holders 41 and 42.

In this case, the samples $S_1$ and $S_2$ are heated at the measurement position, and then the heating furnace 3 is advanced toward the tip end side of the furnace tube 9. Accordingly, the furnace tube 9 can maintain its heated state for a given period due to the remaining heat, and hence it is possible to observe the samples $S_1$ and $S_2$ which are held substantially in the state when the heating is performed.

In this embodiment, the rear end side of the furnace tube 9 is covered with the copper heat conductive member 50, and a part of the heat conductive member 50 is cut out so that the upper half of the furnace tube 9 is exposed at the position corresponding to the sample holders 41 and 42, to thereby form a window W. Further, as illustrated in the sectional view of FIG. 5, the tip end side of the heat conductive member 50 is covered with the rear end portion of the heating furnace 3 at the sample observation position.

Figure 5:
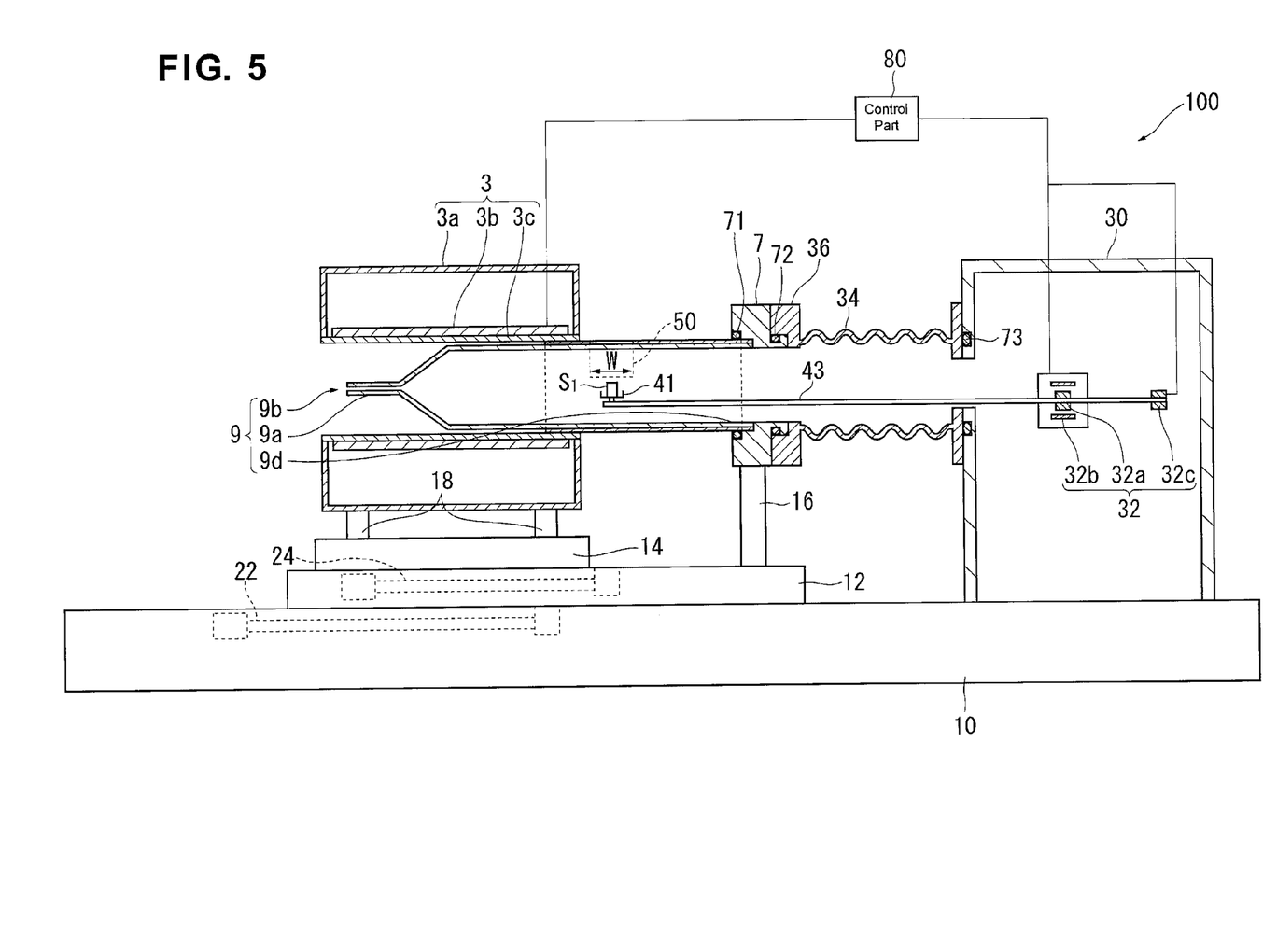
FIG. 5 is a sectional view taken along the line B-B of FIG. 4.

Therefore, the heat of the heating furnace 3 is transferred from the tip end side of the heat conductive member 50, which is covered with the heating furnace 3, to the exposed portion of the furnace tube 9, and hence the samples $S_1$ and $S_2$ can be observed while maintaining the heated state. In particular, it is preferred that the heat conductive member 50 have a thermal conductivity of 50 W/(m·K) or more. As a material having a thermal conductivity of 50 W/(m·K) or more, Cu, Ag, Au, Pt, and the like may be used. Specifically, a heat conductive member 50 which is made of Cu and subjected to Ni plating on any one of its surfaces to prevent oxidation is preferred in terms of cost. Alternatively, a material having high thermal conductivity (for example, any materials described above) may be used only for a part of the heat conductive member 50 which comes into contact with the heating furnace 3 and the furnace tube 9 and requires thermal conduction therebetween, and a material having low thermal conductivity other than the above-mentioned material may be used for a part other than the above. Note that, the heat conductive member 50 only needs to cover at least a part of the exposed portion of the furnace tube 9. Further, a heat conductive member 50 which is removable from the furnace tube 9 is preferred because the heat conductive member 50 can be removed to support a general thermal analysis for performing measurement at temperature exceeding the heat-resistant temperature of the heat conductive member 50.

Figure 6:
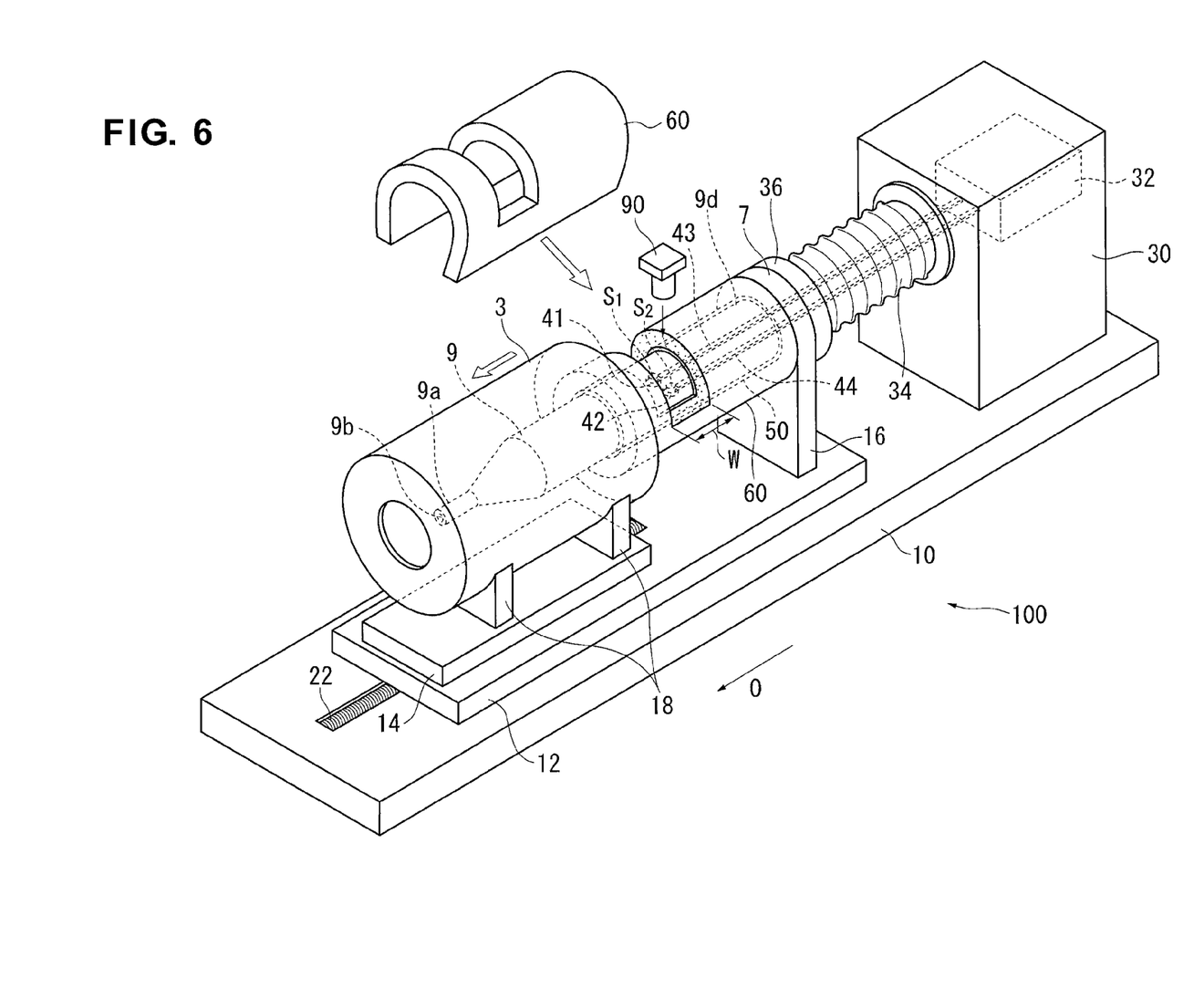
FIG. 6 is a perspective view illustrating an embodiment in which a heat conductive member is covered with a heat insulating member at the sample observation position.

Further, as illustrated in FIG. 6, when at least a part of the heat conductive member 50 is covered with a heat insulating member 60 at the sample observation position, the temperature of the exposed portion of the furnace tube 9 is not easily lowered, and hence the samples $S_1$ and $S_2$ can be observed while maintaining the heated state with higher reliability. As a material for the heat insulating member 60, for example, a material having heat resistance against high temperature and high processability, such as a ceramic-based fiber sheet, may be used.

Figure 10:
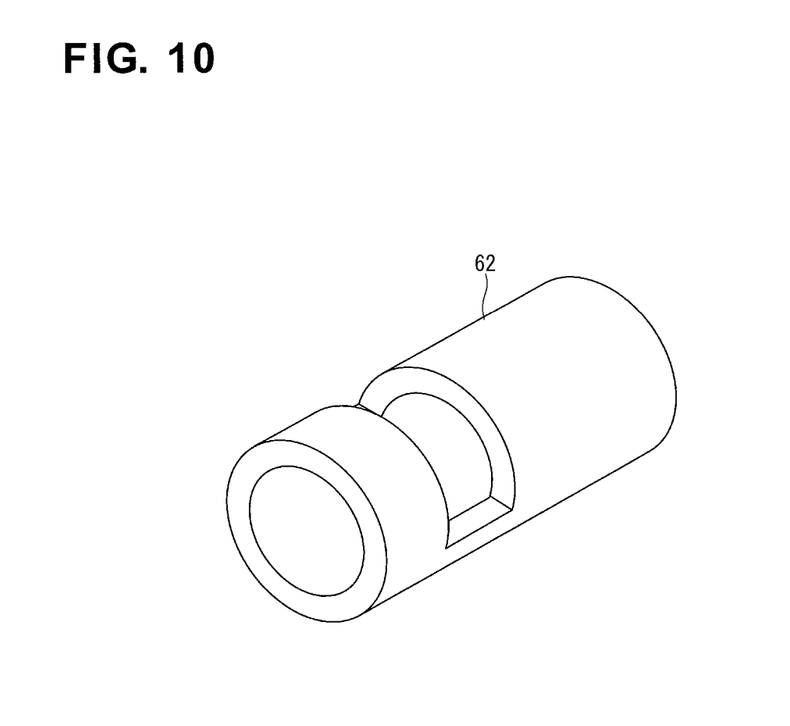
FIG. 10 is a perspective view illustrating a modification example of the heat insulating member.

In the example of FIG. 6, the heat insulating member 60 has a saddle shape (inverted U-shape in cross section), and hence the heat insulating member 60 can cover the furnace tube 9 from above without moving the heating furnace 3 forward and pulling out the heating furnace 3 from the furnace tube 9. The shape of the heat insulating member is not limited to that in the example of FIG. 6. For example, as illustrated in FIG. 10, a heat insulating member 62 having a cylindrical shape in cross section may be employed, and after the heating furnace 3 is moved forward and pulled out from the furnace tube 9, the furnace tube 9 may be inserted from its tip end side into the heat insulating member 62.

Figure 7:
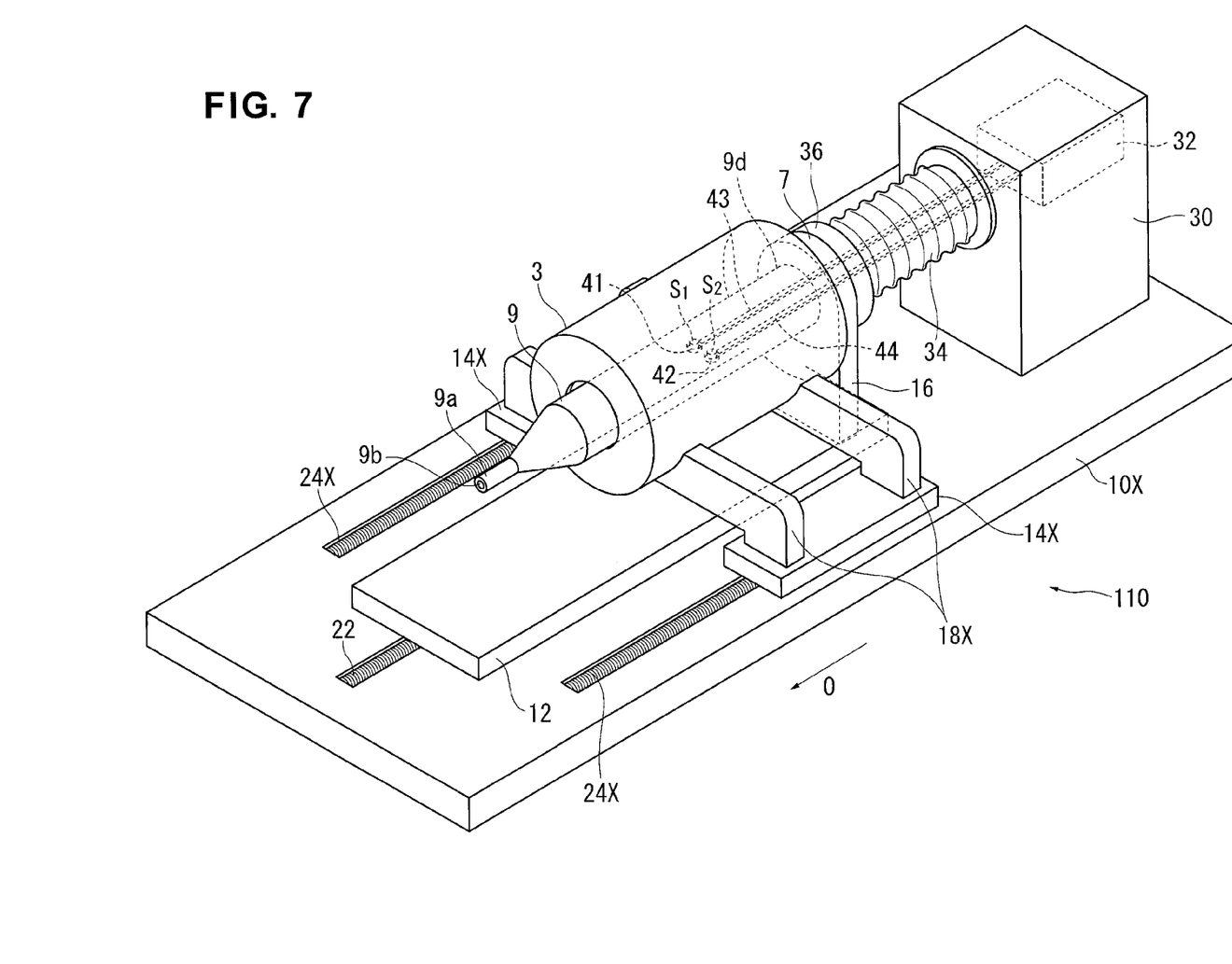
FIG. 7 is a perspective view illustrating a modification example of the thermal analyzer.

FIG. 7 illustrates a modification example of the thermal analyzer, which is a thermal analyzer 110 including a base 10x, second support bases 14x, support columns 18x, and linear actuators 24x which are different in structure from the base 10, the second support base 14, the support columns 18, and the linear actuator 24 of the thermal analyzer 100.

In FIG. 7, two support columns (corresponding to the "heating furnace fixing part" in the claims) 18x extend astride the first support base in a direction perpendicular to the axial direction O from the lower end of the heating furnace 3 in the vicinity of both axial ends thereof. Further, the second support bases 14x are arranged at two locations on the base 10x across the first support base in the direction perpendicular to the axial direction O, and both ends of each support column 18x are connected to the top surfaces of both the second support bases 14x. Note that, the support column 18x on the rear end side is arranged on the tip end side with respect to the support column 16, and does not interfere with the support column 16.

Further, two grooves corresponding to the respective second support bases 14x are formed in the base 10x along the axial direction O, and the linear actuators 24x are arranged in the grooves, respectively. The rear end side of each linear actuator 24x is connected to the corresponding second support base 14x, and the tip end side (or servomotor on the tip end side) is connected to the base 10x. Each second support base 14x is reciprocable by the corresponding linear actuator 24x in the axial direction O.

Also in the thermal analyzer 110, the first support base 12 and the second support bases 14x are configured to move corresponding to the above-mentioned measurement position, sample setting position, and sample observation position.

Note that, at the measurement position and the sample setting position, the first support base 12 and the second support bases 14x are moved independently of each other by the linear actuators 22 and 24x. Therefore, the linear actuators 22 and 24x both correspond to the "first movement means" in the claims.

Further, at the sample observation position, the second support bases 14x are moved by the respective linear actuators 24x. Therefore, the linear actuators 24x also correspond to the "second movement means" in the claims.

The present invention is not limited to the embodiment described above, and encompasses various modifications and equivalents within the spirit and scope of the present invention.

For example, the structures and arrangement states of the first support base, the second support base, the furnace tube fixing part, and the heating furnace fixing part are not limited to the examples described above. Similarly, the structures and arrangement states of the first movement means and the second movement means are not limited to the examples described above.

Further, the thermal analyzer according to the present invention is applicable not only to the above-mentioned thermogravimetry (TG) apparatus, but also to all such thermal analyses defined in JIS K 0129:2005 "General rules for thermal analysis," for measuring physical properties of a measurement target (sample) obtained when the temperature of the sample is controlled based on a program. Specifically, the thermal analyses are typified by the following five methods: (1) Differential Thermal Analysis (DTA) for detecting a temperature (temperature difference), (2) Differential Scanning calorimetry (DSC) for detecting a heat flow difference, (3) Thermogravimetry (TG) for detecting a mass (weight change), (4) Thermomechanical Analysis (TMA) for detecting mechanical characteristics, and (5) Dynamic Mechanical Analysis (DMA).

What is claimed is:

1. A thermal analyzer, comprising:
   a furnace tube which is made of a transparent material and is formed into a cylindrical shape, the furnace tube having a gas discharge port which is reduced in diameter and is arranged at a tip end portion thereof in an axial direction;
   a heating furnace which has a cylindrical shape and externally surrounds the furnace tube;
   sample holding means for holding a sample, the sample holding means being arranged inside the furnace tube;
   a first support base;
   a second support base;
   a furnace tube fixing part for fixing a rear end portion of the furnace tube in the axial direction to the first support base;
   a heating furnace fixing part for fixing the heating furnace to the second support base;
   a measurement chamber which is hermetically connected to the rear end portion of the furnace tube;
   measurement means for measuring a change in physical properties of the sample, the measurement means being arranged inside the measurement chamber;
   first movement means for moving the first support base and the second support base between a measurement position, at which the rear end portion of the furnace tube is connected to the measurement chamber and the sample holding means is covered with the heating furnace, and a sample setting position, at which the furnace tube and the heating furnace are advanced toward a tip end side with respect to the measurement position and the sample holding means is exposed on a rear end side with respect to the furnace tube and the heating furnace; and
   second movement means for moving only the second support base to a sample observation position, at which the heating furnace is advanced toward the tip end side with respect to the measurement position under a state in which the rear end portion of the furnace tube is connected to the measurement chamber,
   and the furnace tube is exposed in a region including the sample holding means,
   the thermal analyzer being configured to enable observation of the sample from outside the exposed furnace tube at the sample observation position.

2. A thermal analyzer according to claim 1, wherein the second support base is placed on the first support base, and when the first movement means moves the first support base, the second support base moves integrally with the first support base.

3. A thermal analyzer according to claim 1, wherein the furnace tube is made of one of quartz glass and sapphire glass.

4. A thermal analyzer according to claim 1, further comprising a heat conductive member which covers at least a part of the exposed furnace tube at the sample observation position to transfer heat of the heating furnace.

5. A thermal analyzer according to claim 4, wherein the heat conductive member has a thermal conductivity of 50 W/(m·K) or more.

6. A thermal analyzer according to claim 4, further comprising a heat insulating member which covers at least a part of the heat conductive member.

* * * * *